United States Patent
Tormod (10) Patent No.: US 8,649,005 B2
(45) Date of Patent: Feb. 11, 2014

(54) OPTICAL FLOW CELL DETECTOR

(75) Inventor: Stig Tormod, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/522,880

(22) PCT Filed: Jan. 26, 2011

(86) PCT No.: PCT/SE2011/050078
§ 371 (c)(1), (2), (4) Date: Jul. 18, 2012

(87) PCT Pub. No.: WO2011/093775
PCT Pub. Date: Aug. 4, 2011

(65) Prior Publication Data
US 2012/0327397 A1    Dec. 27, 2012

(30) Foreign Application Priority Data

Jan. 28, 2010 (SE) ........................ 1050090

(51) Int. Cl.
*G01N 1/10* (2006.01)
(52) U.S. Cl.
USPC .................................................. 356/246
(58) Field of Classification Search
USPC .................................................. 356/246
See application file for complete search history.

(56) References Cited

U.S. PATENT DOCUMENTS

| | | | |
|---|---|---|---|
| 5,140,169 A * | 8/1992 | Evens et al. | 250/576 |
| 5,423,513 A * | 6/1995 | Chervet et al. | 250/227.25 |
| 6,266,139 B1 | 7/2001 | Mannhardt | |
| 6,600,558 B2 * | 7/2003 | Ueno et al. | 356/246 |

FOREIGN PATENT DOCUMENTS

WO   WO 2008/132611   11/2008

OTHER PUBLICATIONS

Flowers, P., et al., Analytical Chemistry, 68, (1996), 199-202.
Lacki, P., et al., Eurosensors. Proceedings of the European Conference on Solid-State Transducers and the UK Conference on Sensors and Their Applications, 1, (1998), 343-346.

* cited by examiner

*Primary Examiner* — Tu Nguyen (57) ABSTRACT

Optical flow cell detector comprising a sample inlet and outlet in fluidic communication through a flow cell channel of cross sectional area A, an input light guide with an light exit surface arranged adjacent and in optical alignment with a light entrance surface of an output light guide, wherein the input light guide and the output light guide protrudes into the flow cell channel and wherein the distance between the light exit surface and the light entrance surface is less than 1.0 mm, and wherein the cross sectional area of the protruding portions of the input light guide and the output light guide in the flow direction is less than A/2.

10 Claims, 10 Drawing Sheets

OPTICAL FLOW CELL DETECTOR

CROSS-REFERENCE TO RELATED APPLICATIONS

This application is a filing under 35 U.S.C. 371 of international application number PCT/SE2011/050078, filed Jan. 26, 2011, published on Aug. 4, 2011 as WO 2011/093775, which claims priority to application number 1050090-8 filed in Sweden on Jan. 28, 2010.

FIELD OF THE INVENTION

The present disclosure relates to an optical flow cell detector, and a flow cell absorption monitor system comprising such a sensor.

BACKGROUND OF THE INVENTION

A flow cell absorption monitor system, typically comprises a light source for providing light of one or more wavelengths to a fluid sample in a fluid cell and an optical detection system for detecting any interaction between the light and the sample. One example of a flow cell absorption monitor system is a flow cell UV absorption monitor system that is utilized to measure different absorbance of light at various wavelengths in chromatography systems when separated molecules are eluted from the columns.

Monitor systems of this type usually include a light source, a flow cell and a light detector. Ideally, the flow cell is designed to ensure a signal-to-noise ratio with minimal drift and refractive index sensitivity.

There is an increasing demand for the ability to measure high protein concentrations, far beyond where traditional UV detector flow cells are applicable. The reasons for the demand is partially driven by higher titers and more efficient downstream processing and can be as simple and straight-forward as a wish to determine the concentration of protein pools without having to dilute the sample. There has been expressed a desire to measure up to 100-200 mg/ml in hold tanks associated with chromatography.

SUMMARY OF THE INVENTION

The object of the invention is to provide a new optical flow cell detector and a flow cell absorption monitor system using the same, which overcomes one or more drawbacks of the prior art. This is achieved by the optical flow cell detector and the flow cell absorption monitor system as defined in the independent claim.

One advantage with such an optical flow cell detector is that it is capable of registering high protein concentrations in a flow through mode, and with an essentially linear response.

Another advantage is that the detector may be arranged in the main flow channel as it may be designed such that the cross sectional flow area is essentially uniform in the flow direction throughout the flow cell.

Further scope of applicability of the present invention will become apparent from the detailed description given hereinafter. However, it should be understood that the detailed description and specific examples while indicating preferred embodiments of the invention are given by way of illustration only. Various changes and modifications within the spirit and scope of the invention will become apparent to those skilled in the art from the detailed description below.

BRIEF DESCRIPTION OF DRAWINGS

These and other advantages of the present invention will become more apparent as the following description is read in conjunction with the accompanying drawings, wherein.

DETAILED DESCRIPTION OF THE PREFERRED EMBODIMENTS

The presently preferred embodiments of the invention are described with reference to the drawings, where like components are identified with the same numerals. The descriptions of the preferred embodiments are exemplary and are not intended to limit the scope of the invention.

Figure 1:
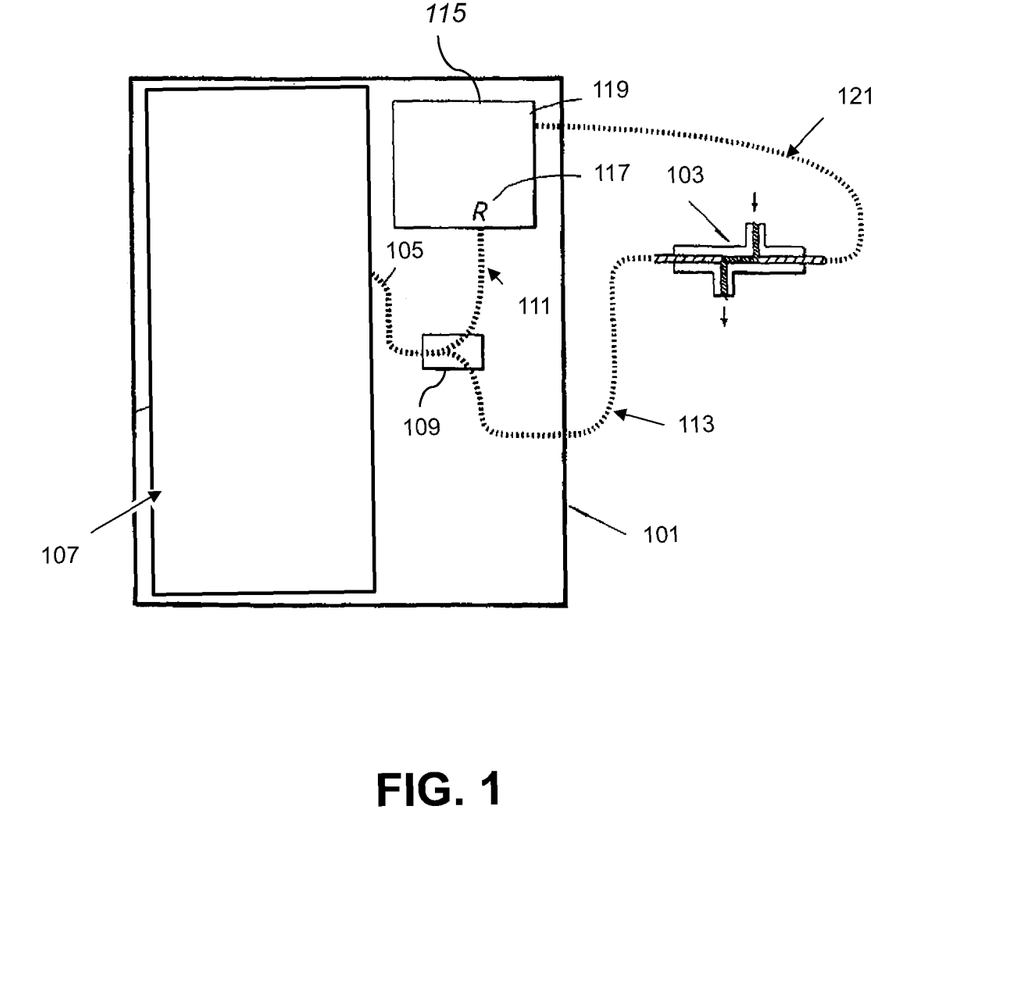
FIG. 1 illustrates a schematic of a typical flow cell absorption monitor system.

FIG. 1 illustrates a one embodiment of a flow cell absorption monitor system, such as a multi-wavelength Ultra-violet (UV)-Visible monitor. This monitor 101 includes an interchangeable flow cell 103 and optical fibers 105 connecting the flow cell to the monitor unit 101. Monitor 101 may e.g. be a Monitor UV-900 manufactured by GE Healthcare, Life Sciences located in Uppsala, Sweden. This monitor utilizes advanced fiber optic technology to monitor light with high sensitivity at up to three wavelengths simultaneously in a range of 190-700 nm. The use of fiber optics together with the unique flow cell design ensures a signal-to-noise ratio with minimal drift and refractive index sensitivity. Typically, the monitor 101 includes a monochromator 107 with a light source (not shown), such as a xenon flash lamp (not shown) that provides a high intensity, continuous spectrum of light, and a tuneable monochromator arrangement (not shown) for selecting the wavelength of light output to the fiber 105. The lamp is activated only during the chromatographic run, ensuring that its long lifetime of approximately 4000 hours of effective operation is used efficiently. However, the tuneable monochromator, may be any suitable type, capable of providing the desired wavelength range, or even two or more units with complementary wavelength ranges. In one embodiment, the tuneable monochromator is a tuneable laser unit capable of providing monochromatic light over a specified range. In some embodiments, when tuneability is of less importance, the tuneable monochromator may be substituted by one or more discrete monochromatic light sources. In another embodiment, the monochromator is replaced by a broad band light source, and a light detection unit 115 is e.g a spectrometer capable of spectroscopiaclly dividing the received spectra. In the disclosed monitor 101, the optical fiber 105 optics leads the light from the monochromator 107 to an optical splitter unit 109 splitting the light to a reference fiber 111 and a flow cell fiber 113 leading directly to the flow cell 103 and focus its full intensity on the liquid flow path, thus maximizing the sensitivity of the monitoring. Flow cell 103 may have any path length, such as a path length of 2 mm and cell volume of 2 μl or path length of 10 mm and a cell volume of 8 μl. The transmitted light through the flow cell 103 is guided to a light detection unit 115 via an optical fiber 121. The light detection unit 115 has a flow cell input 119 connected to fiber 121 and a reference input 117 connected to the reference fiber 111. The detection unit 115 further may comprise suitable processing means for comparing the flow cell input with the reference to detect changes in light absorption in the flow cell.

Figure 2A:
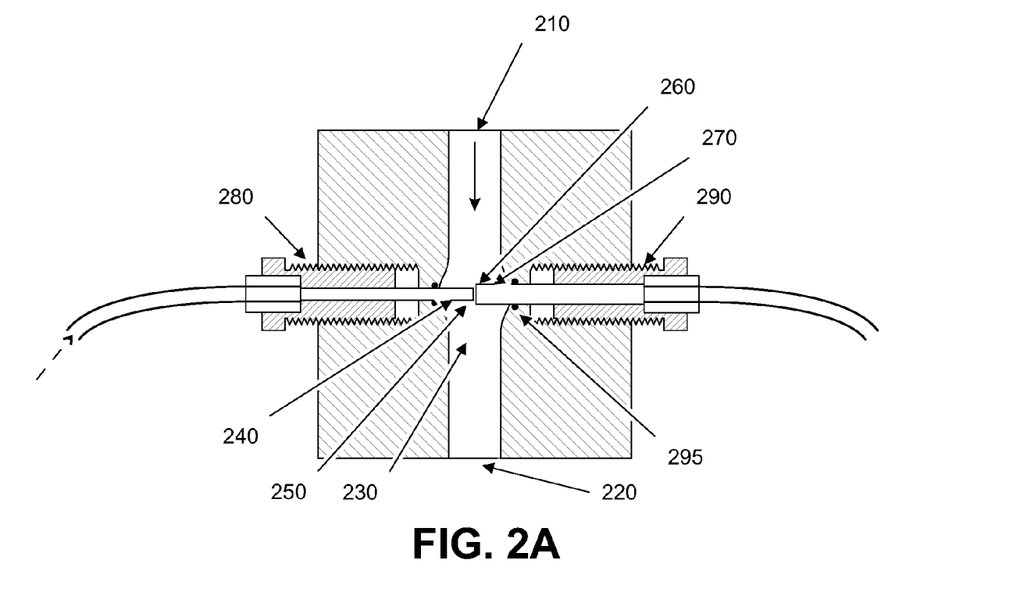
FIGS. 2A to 2C show a schematic optical flow cell detector in accordance with an embodiment of the invention.
Figure 2B:
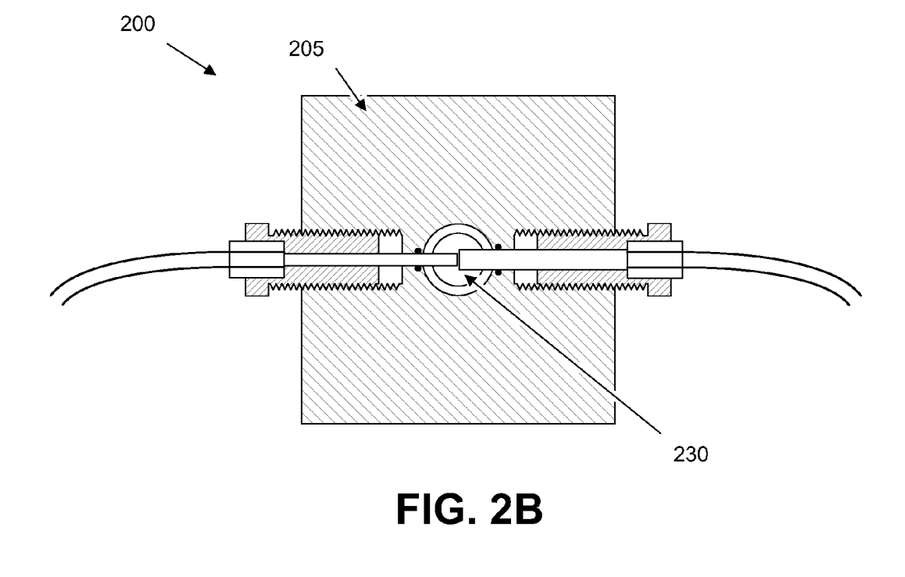

FIGS. 2A and 2B show a schematic optical flow cell detector 200 in accordance with an embodiment of the invention. The optical flow cell detector 200 comprises a detector body 205 with a sample inlet 210 and outlet 220 in fluidic communication through a flow cell channel 230 of cross sectional area A. The flow cell channel 230 may essentially be of any cross sectional area A as required for the specific application where it is to be used, depending on factors as flow rate, viscosity etc. In the disclosed embodiment, the cross sectional shape is circular which is beneficial from a manufacturing point of view as well as a fluid flow point of view, but it may actually be of essentially any suitable shape as long as the fluid flow characteristics are preserved within the desired range.

The detection optics is comprised of an input light guide 240 with a light exit surface 250 arranged adjacent and in optical alignment with a light entrance 260 surface of an output light guide 270. As is disclosed, the input light guide 240 and the output light guide 270 protrudes into the flow cell channel 230 so that the optical gap between the light exit surface 250 and the light entrance surface 260 is situated centrally in the flow cell channel 230. The optical gap, may e.g. be situated at any position in the flow cell channel 230 as long as it is not located in a stagnant zone, e.g. adjacent a wall of the channel in order to ensure that the fluid in the gap is representative of the fluid flow. In the disclosed embodiment, the input light guide 240 and the output light guide 270 protrudes essentially transverse into the flow cell channel 230, whereby exchange of fluid in the optical gap is promoted. However, the angular relationship between the fluid flow channel and the light guides 240 and 270 need not be transverse, but can be any suitable angle and configuration provided that desired renewal of the fluid in the optical gap is achieved. In alternative embodiments, the fluid flow channel 230 need not be straight, but it may be curved or the like.

It has surprisingly been found that the present approach with relatively small sized light guides 240 and 270 protruding into the fluid flow channel 230 provides excellent capability of measuring high concentrations of e.g. proteins in the flow when arranged at a short distance from each other such as 0.5 mm or less. As will be discussed in more detail below, a high degree of linearity for high concentrations has been disclosed for embodiments with an optical gap of 0.12 and 0.07 mm. The optical gap is selected depending on the concentration range to be measured, and it may e.g be any value from 0.02 to 1 mm such as 0.7, 0.5, 0.4, 0.3, 0.2, 0.1, 0.07, 0.05 mm or there between. It has been found, that the fluid in the optical gap is readily exchanged even at the smallest gaps and at moderate flow rates, which is believed to be a result of the small optical cross sectional area and the "protruded" position of the gap essentially at the center of the fluid flow channel.

In the embodiment of FIGS. 2A and 2B, the optical gap is adjustable in that the light guides 240 and 270 are arranged in threaded ferrules 280 and 290 respectively, and the optical gap may be adjusted by turning the ferrules 280 and 290. In FIGS. 2A and 2B, the light guides 240 and 270 are sealed from the fluid flow channel by seals 295 e.g. in the form of O-rings or the like, to avoid fluid form exiting there through.

Figure 2C:
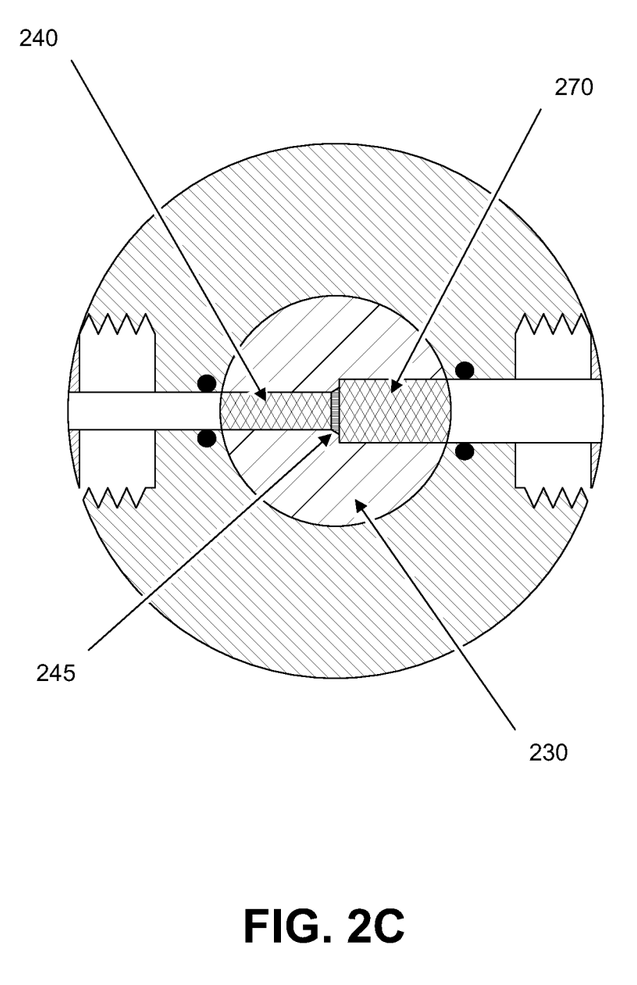

As is mentioned, it is believed to be essential to avoid disruption of the fluid flow, whereby a small cross sectional area of the protruding portions of the light guides and the output light guide in the flow direction is essential, and in the disclosed embodiments the total cross sectional area of the protruding portions of the input and output light guides 240, 270 is less than about A/2, or even A/4 in the flow direction. FIG. 2C shows an enlargement of the flow cell channel 230 region of the flow cell detector 200 of FIGS. 2A and 2B, wherein the area A of the flow cell channel 230 is filled by a broad diagonal pattern and the protruding portions of the input and output light guides 240, 270 are filled by a rombohedric pattern. From FIG. 2c it is clear that the uninterrupted area of the flow cell channel 230 is essentially larger than the total area of the protruding light guides 240 and 270, whereby the fluid flow in the flow cell channel will be relatively uninterrupted. As mentioned the dimensions of the protruding sections of the input and output light guides 240, 270 may be designed in any suitable way to achieve a small cross sectional area compared to the area A of the flow channel 230, whilst providing rigid positioning of the optical end-surfaces of the input and output light guides 240, 270 respectively, in order to achieve desired optical transmittance there between. In FIG. 2C the optical cross sectional area or the "detection area" between the input and output light guides 240, 270 is indicated by dashed region 245. As is concluded elsewhere, the optical cross sectional area 245 in the present flow cell detector 200 is very small compared to the total area A of the flow channel 230, e.g. less than A/50, A/100, A/200, A/1000 or less. However, the present light guide type design ensures a high light flux in the small optical cross sectional area 245 (volume).

The light guides may be comprised of any suitable optical material capable of transmitting light, such as glass, quarts, light transmitting polymers etc. One or both may be provided with an optically blocking sleeve or coating (not shown) at the peripheral surface to avoid leakage of light. According to one embodiment, the light guides 240 and 270 are cylindrical with a diameter of 5 mm or less, e.g. 3 mm, or 1 mm or the like. The diameter of the light guides 240 and 270 obviously depends on the total area A of the flow channel 230. According to one embodiment, schematically disclosed in FIGS. 2A and 2B, the cross sectional flow area of the fluid flow channel may be essentially uniform in the flow direction throughout the flow cell. In the disclosed embodiment, the reduced cross sectional flow area due to the protruding light guides 240 and 270 is compensated by a local widening of the fluid flow channel. This is particularly useful for flow cells with a relatively small fluid flow channel compared to the protruding light guides, but in other embodiments no compensation may be needed.

As can be seen in FIGS. 2A and 2B, the light guides 240 and 270 may be asymmetric in core size, with the input light guide being thinner than the output wave guide, in order to capture essentially the whole cone of light (its numerical aperture) emerging from the light exit surface at the light entrance surface 260.

In the embodiment of FIGS. 2A and 2B, the light guides 240 and 270 are shown in optical contact with optical fibers 113 and 121 respectively, in turn connected to a monitor unit 101 (not shown). However, one or both of the light guides 240 and 270 may be direct coupled to the optical detection system of the flow cell monitor system 101.

Figure 4:
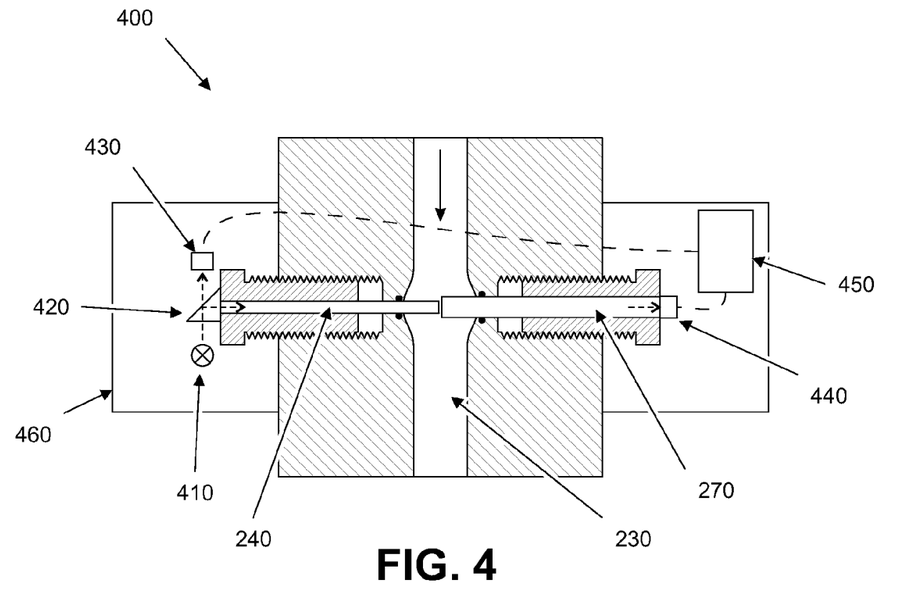
FIG. 4 shows a schematic embodiment of an integrated flow cell absorption monitor system with an optical flow cell detector in accordance with an embodiment of the invention.

As is shown in FIG. 4, the optical flow cell detector 200 may be designed as an integrated flow cell light absorption monitor system 400, wherein a light source 410 is arranged to illuminate a prism 420 that split the light into a reference beam that is directed to a reference light sensor 430 and a sample beam, directed into the inlet light guide 240. A sample light sensor 440 is arranged to receive light from the output light guide 270. The integrated monitor system 400 further comprises a control unit for receiving output signals from the light sensors 430 and 440 and to compare and potentially perform calculations of the signals. The components may be protected by a housing 460.

Figures 3A, 3B:
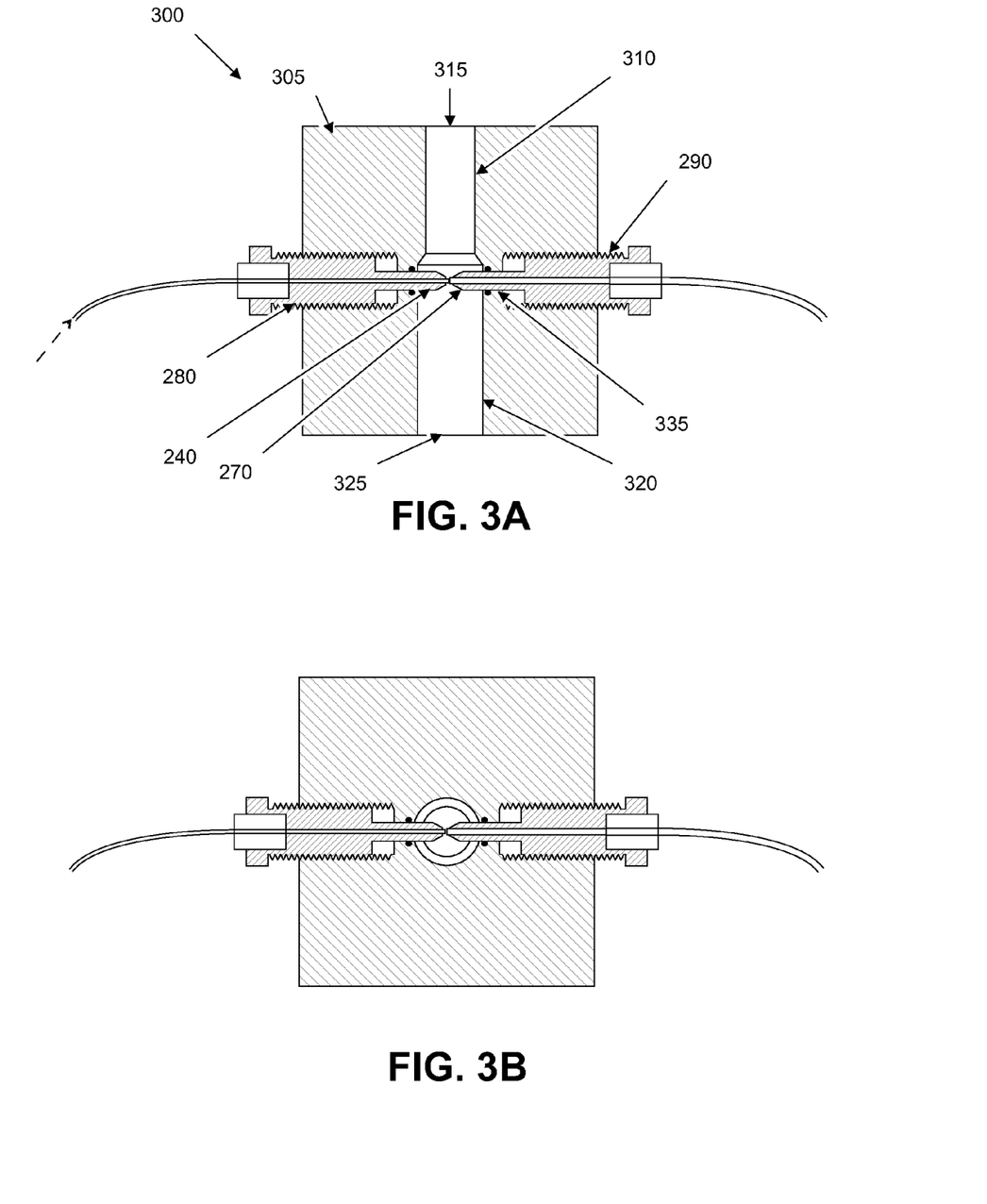
FIGS. 3A to 3C show a schematic optical flow cell detector in accordance with an embodiment of the invention.
Figure 3C:
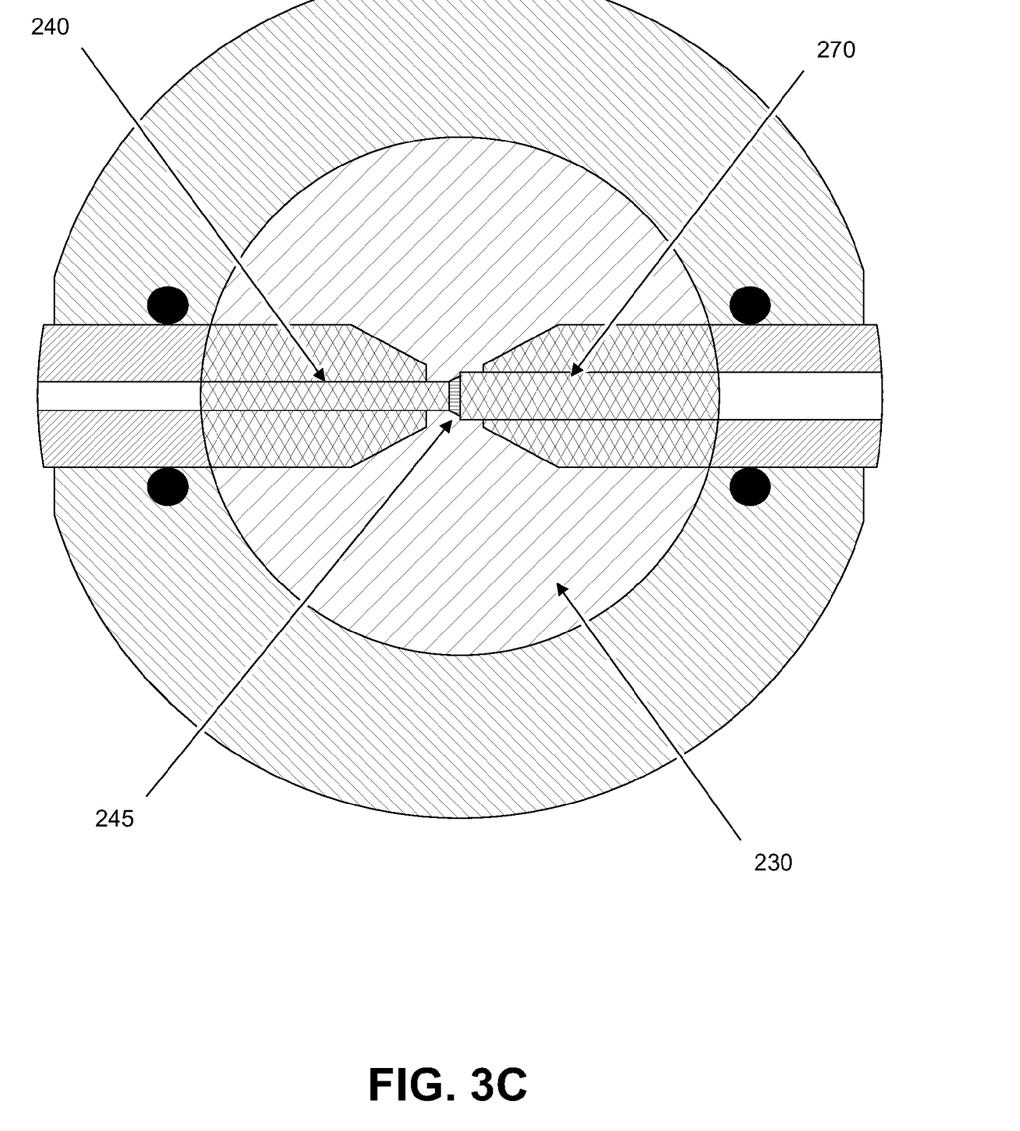

FIGS. 3A and 3B show a schematic optical flow cell detector 300 in accordance with an embodiment of the invention. This optical flow cell detector 300 comprises a detector body 305 with a first bore 310 extending from an external surface of the detector body 300 forming the sample inlet 315, a second bore 320, concentric with and wider than the first bore 310, extending from the first bore to an external surface of the detector body 300 forming the sample outlet 325. Together, the first and the second bores form a fluid flow channel 330. It further comprises a third bore 335 extending through the detector body 300 and crossing the second bore 320, and the input light guide 240 and the output light guide 270 are arranged in opposing sections of the third bore 335 such that they protrude into the second bore 320. In this embodiment, the light guides 240 and 270 are arranged in support ferrules 280 and 290 that are extended into the fluid flow channel 330 to support the thin light guides 240 and 270, whereby the waveguides may be comprised of thin light guiding elements, such as optic fibers or the like. According to one embodiment, the diameter of the input and output light guides 240 and 270 is less than 2 mm, such as 1 mm, 0.8 mm, 0.5 mm or the like. According to one embodiment, the input light guide 240 is comprised of an optic fiber with a core diameter of about 400 µm and the output light guide 240 is comprised of an optic fiber with a core diameter of about 600 µm. By using such thin light guides 240 and 270, a very small optical cross sectional area 245 with high light flux is achieved. FIG. 3c shows an enlargement of the flow cell channel 230 region of the flow cell detector 200 of FIGS. 3A and 3B, wherein it can be seen that the resulting optical cross sectional area 245 in the present flow cell detector 200 can be made even smaller in this embodiment.

Figure 5:
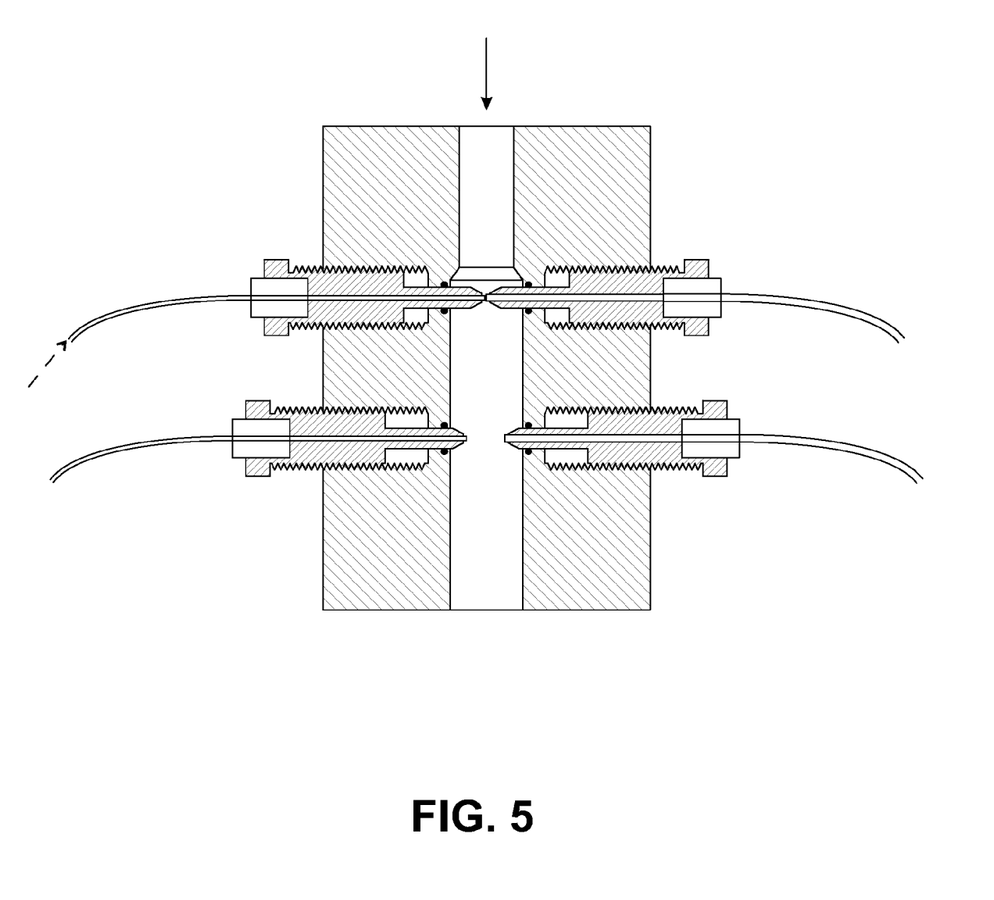
FIG. 5 shows a schematic optical flow cell dual detector in accordance with an embodiment of the invention.
Figure 6:
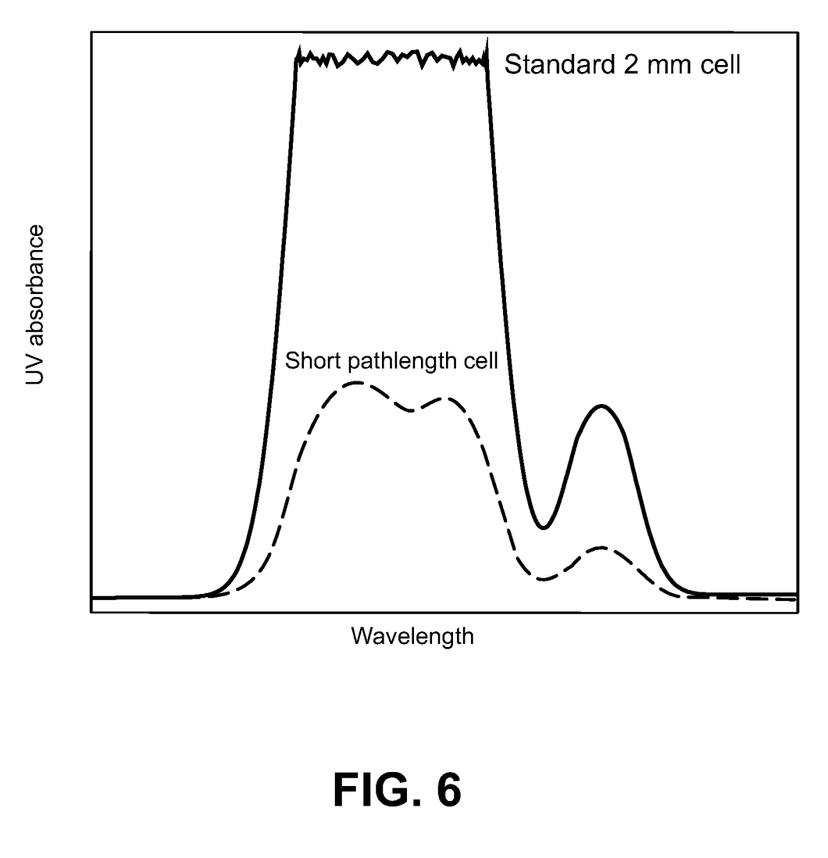
FIG. 6 shows a schematic UV absorption graph for an optical flow cell detector in accordance with an embodiment of the invention, in comparison with a schematic graph for a prior art wide gap detector.

By combining the output from a narrow optical gap detector according to the present invention and a wide optical gap detector, both high concentration capability and high sensitivity can be achieved. FIG. 5 shows a schematic optical flow cell dual detector in accordance with an embodiment of the invention. The contributions from the two different type of detectors are illustrated in FIG. 6 which shows a schematic UV absorption graph for an optical flow cell detector in accordance with an embodiment of the invention, in comparison with a schematic graph for a prior art wide gap detector. As can be seen in FIG. 6, the signal from the wide gap detector is saturated well before the double peak is reached and information regarding the double peak shape and position is not registered. For the small gap detector according to the present invention, the full double peak is registered, but the sensitivity at lower concentrations is may be somewhat reduced.

As is indicated above, the ability to measure high concentrations of proteins is highly desirable in many situations, such as:

Chromatogram review processes and process troubleshooting based on characterization of peak shapes will require an accurate representation of peak shapes and thus a linear response up to peak apex.

There is a current trend towards direct coupling of two or more unit operations with possible sample conditioning in-between. Regulatory authorities may require a true "process fingerprint" in the form of an accurate on-line chromatogram of the sample between the two unit operations. Such a process consistency fingerprint requires a detector that is linear up to the highest peak concentration.

In continuous chromatography, several identical columns are connected in an arrangement that allows columns to be operated in series and/or in parallel, wherein individual columns according to the prior art are connected or disconnected for elution using time-based valve-switching. Recently, a effluent-signal based switching approach has been suggested in SE0950494-5 by the same applicant, wherein an effluent signal, e.g. an UV absorbance signal, representative of the composition of the effluent from the column is detected and the valve-switching controlled based on the detected signal. The small gap detector according to the present invention will allow detection of the breakthrough for modern high-titer feeds.

Measurement of high protein concentrations on-line during ultra-filtration/Dia-filtration (UF/DF) in the final formulation step.

EXPERIMENTS

Figure 7:
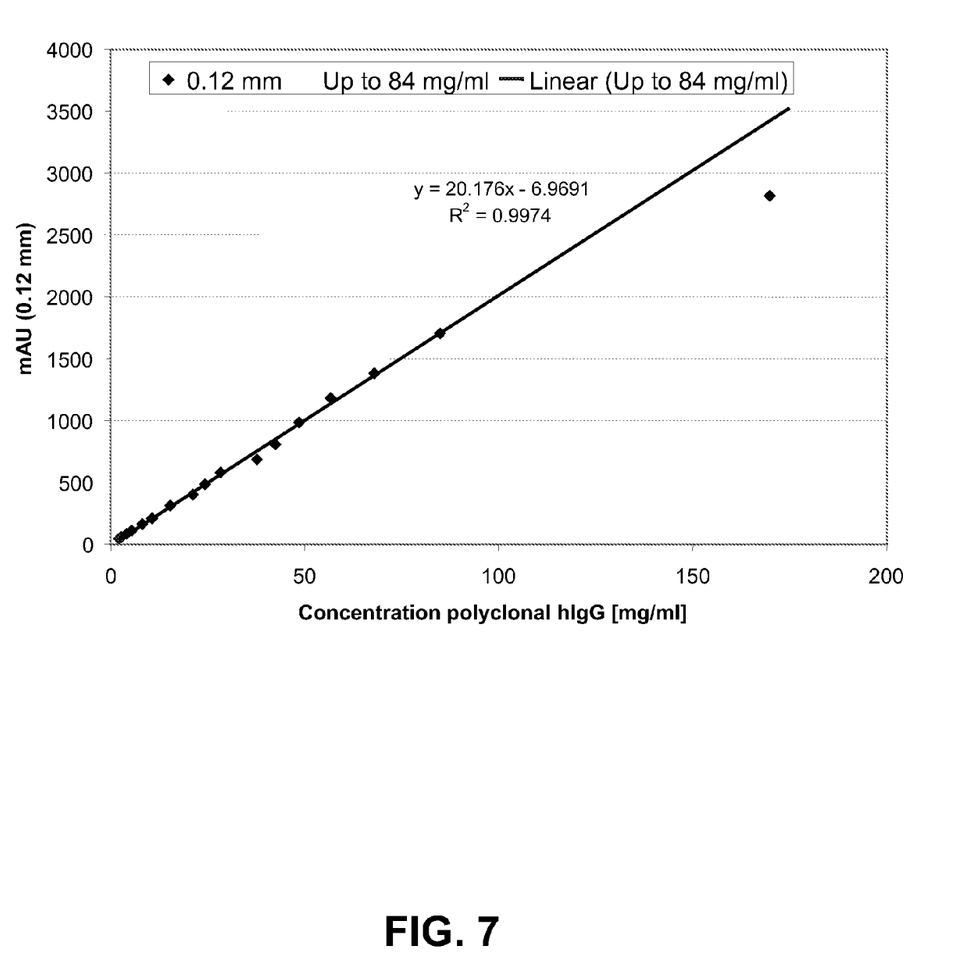
FIG. 7 is an experimental graph showing the linearity of a optical flow cell detector in accordance with an embodiment of the invention.

FIG. 7 is an experimental graph showing the linearity of a optical flow cell detector in accordance with an embodiment of the invention. In the experiments, a prototype optical flow cell detector with 0.12 mm path length was subsequently tested with a dilution series of polyclonal hIgG (starting at 165 mg/ml) showing linearity up to at least 84 mg/ml.

Figure 8:
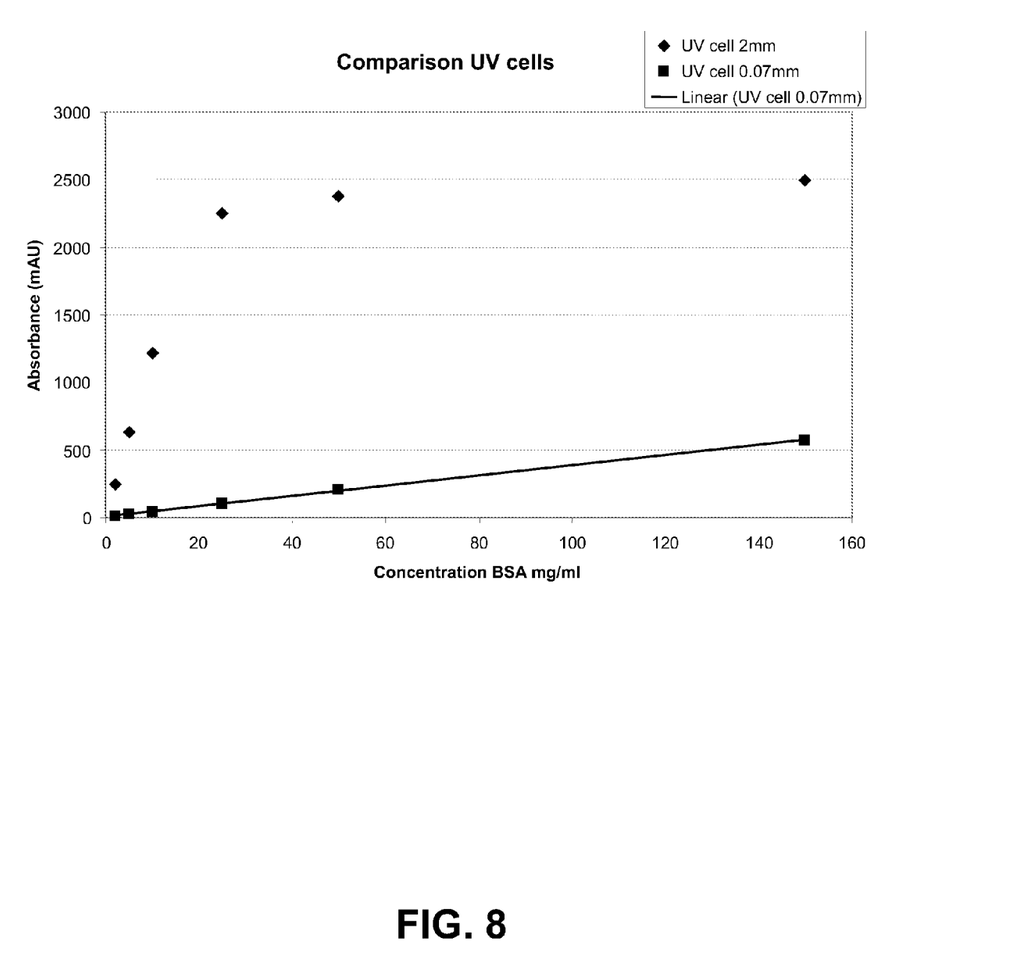
FIG. 8 is an experimental graph showing the linearity of a optical flow cell detector in accordance with an embodiment of the invention in comparison with a prior art wide gap detector.

FIG. 8 is an experimental graph showing the linearity of a optical flow cell detector in accordance with an embodiment of the invention in comparison with a prior art wide gap detector. The prototype cell was reconfigured to 0.07 mm path length and tested with a dilution series of BSA up to 150 mg/ml and compared to a 2 mm cell. Linearity up to 150 mg/ml (and probably more than that) was demonstrated for the 0.07 mm cell while the 2 mm cell was linear only up to about 10 mg/ml.

Although the present invention has been described and illustrated in detail, it is to be clearly understood that this is done by way of illustration and example only and is not to be taken by way of limitation. The scope is to be limited only by the terms of the appended claims.

What is claimed is:

1. An optical flow cell detector comprising a sample inlet and outlet in fluidic communication through a flow cell channel of cross sectional area A, an input light guide with an light exit surface arranged adjacent and in optical alignment with a light entrance surface of an output light guide, wherein the input light guide and the output light guide protrudes into the flow cell channel and wherein the distance between the light exit surface and the light entrance surface is less than 1.0 mm, wherein the cross sectional area of the protruding portions of the input light guide and the output light guide in the flow direction is less than A/2, and wherein the input light guide and the output light guide protrudes from a wall of the flow cell channel, at least beyond a stagnant zone.

2. The optical flow cell detector of claim 1, wherein the cross sectional flow area is essentially uniform in the flow direction throughout the flow cell.

3. The optical flow cell detector of claim 1, wherein the distance between the light exit surface and the light entrance surface is adjustable.

4. The optical flow cell detector of claim 1, wherein the light exit surface of the input light guide has a smaller cross sectional area than the light entrance surface of the output light guide.

5. The optical flow cell detector of claim 1, wherein the input light guide and the output light guide are comprised of optical fibers.

6. The optical flow cell detector of claim 1, wherein at least one of the input and output light guides is arranged in a support ferrule that is extended into the fluid flow channel.

7. The optical flow cell detector of claim 1, comprising a second optical detector with a distance between the light exit surface and the light entrance surface exceeding the distance of the first optical detector.

8. The flow cell light absorption monitor system of claim 7, arranged to register the absorption in the UV to visible wavelength range.

9. The optical flow cell detector of claim 1, comprising a detector body with a first bore extending from an external surface of the detector body forming the sample inlet, a second bore, concentric with and wider than the first bore, extending from the first bore to an external surface of the detector body forming the sample outlet, a third bore extending through the detector body and crossing the second bore, the input light guide and the output light guide are arranged in opposing sections of the third bore such that they protrude into the second bore.

10. A flow cell light absorption monitor system comprising a light source, a light detector and the flow cell of claim 1.

\* \* \* \* \*